United States Patent [19]

Schmidt et al.

[11] Patent Number: 4,706,679
[45] Date of Patent: Nov. 17, 1987

[54] DISPOSABLE MONITOR FOR AN EEG HEAD SET

[75] Inventors: Albert L. Schmidt, Murrysville; Gary W. Sherwin, South Huntington; Kenneth K. Blackham, Edgewood; John L. Johnson, Plum Borough, all of Pa.

[73] Assignee: Westinghouse Electric Corp., Pittsburgh, Pa.

[21] Appl. No.: 822,725

[22] Filed: Jan. 27, 1986

[51] Int. Cl.$^4$ .................................................. A61B 5/04
[52] U.S. Cl. .................................................... 128/639
[58] Field of Search ............................... 128/639–644, 128/784–786, 802, 803

[56] References Cited

U.S. PATENT DOCUMENTS

| | | | |
|---|---|---|---|
| 2,549,836 | 4/1951 | McIntyre et al. | 128/644 |
| 3,313,293 | 4/1967 | Chesebrough et al. | 128/642 |
| 4,004,578 | 1/1977 | Palmius | 128/642 |
| 4,202,344 | 5/1980 | Mills et al. | 128/644 |
| 4,534,366 | 8/1985 | Soukup | 128/786 |
| 4,535,779 | 8/1985 | Ober | 128/644 |

FOREIGN PATENT DOCUMENTS

| | | | |
|---|---|---|---|
| 2552035 | 5/1977 | Fed. Rep. of Germany | 128/642 |
| 976954 | 11/1982 | U.S.S.R. | 128/642 |

OTHER PUBLICATIONS

James et al., "Carbon Fibre Microelectrodes", J. Neuroscience Methods, 1, No. 3, 1979, 279–287.

Primary Examiner—Lee S. Cohen
Attorney, Agent, or Firm—Daniel C. Abeles

[57] ABSTRACT

The present invention includes an adjustable head set held in place on the back of a patient's head when the patient leans back against a chair head rest. The head set includes self-preparing disposable monitors that provide good contact with the patient's head without prior skin preparation. The monitors include a conductive tube containing conductive wires, the tips of which form a planar cushion surface for contacting the patient's head through a caratinaceous layer of skin. The monitors are held in adjustable holders that allow the contact force to be adjusted. The adjustable holders are mounted in holder slots of head set springs where the slots also allow adjustment of the placement of the monitors. The springs can include hinges for rotatably adjusting placement of the monitors. The disposable monitors are filled with an electrolyte solution using a disposable applicator including a puncturable film, punctured by a monitor when the electrolyte solution is being applied.

5 Claims, 15 Drawing Figures

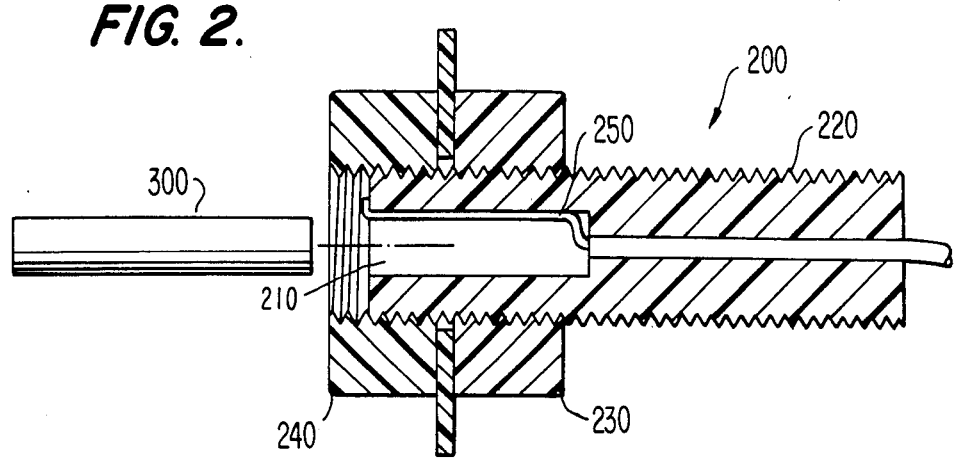
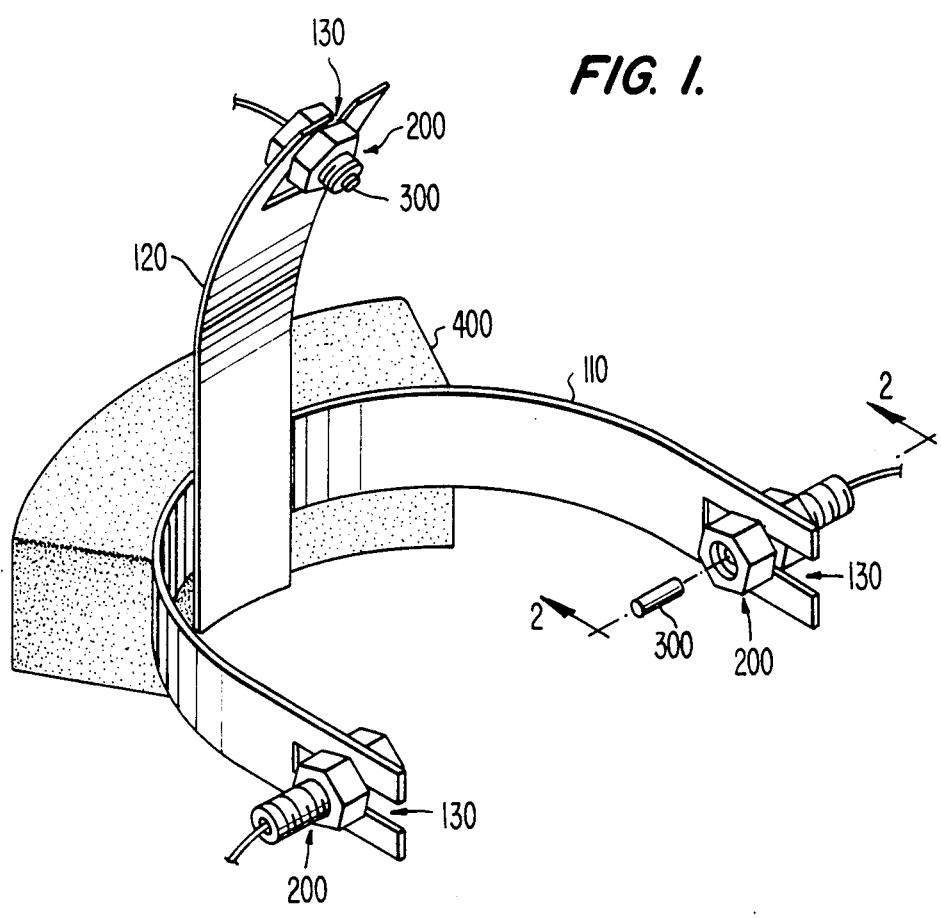

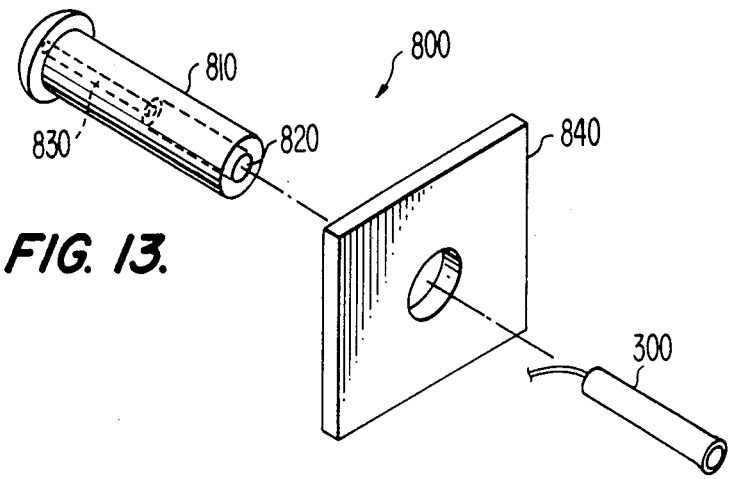
*FIG. 13.*
*FIG. 5.* 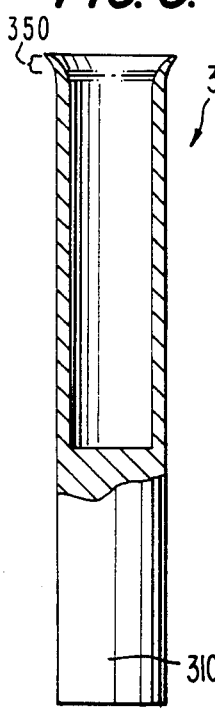 *FIG. 6.* 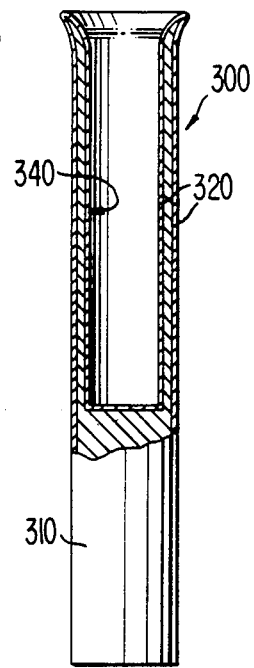 *FIG. 3.* 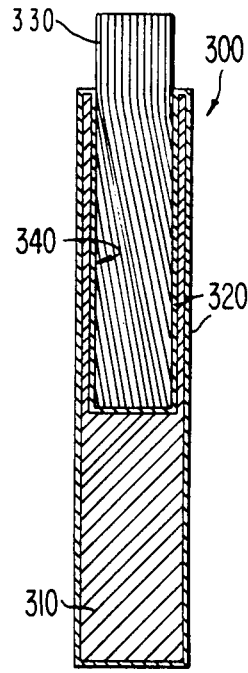 *FIG. 4.* 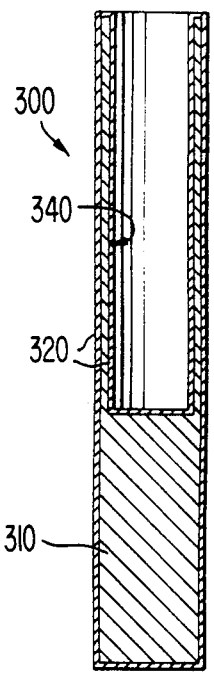
*FIG. 14.*
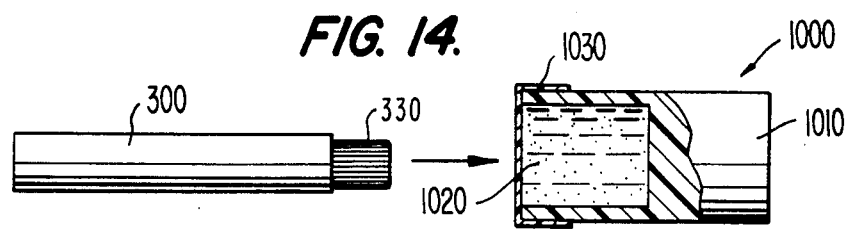

DISPOSABLE MONITOR FOR AN EEG HEAD SET

CROSS REFERENCES TO RELATED APPLICATIONS

This application is related to pending U.S. applications having Ser. Nos. 727,060; 727,032; and 727,031 and U.S. Pat. Nos. 4,640,290 and 4,632,120 assigned to the assignee of the present invention.

BACKGROUND OF THE INVENTION

1. Field of the Invention

The present invention is directed to an electroencephalographic (EEG) head set and disposable EEG monitors mounted in the head set and, more particularly, to a head set which is applied to a patient's head, includes self-preparing disposable monitors which contact a blood rich epidermis layer under a caratinaceous cuticle layer or dead layer of skin so that EEG measurements can be made and is accompanied by a disposable electrolyte applicator for the monitors.

2. Description of the Related Art

Conventional EEG electrodes come in the form of stick-on electrodes or stretch caps with electrodes mounted therein. The conventional electrodes require that the skin adjacent to the contact surface of the electrode be cut to remove the electrically insulating caratinaceous layer of skin. In addition, when these electrodes are applied to the head, the hair around the contact pointed must also be cut and an electrolyte cream applied to the scalp. These electrodes are called conventional non-self-preparing electrodes because the skin of the patient must be prepared before the electrode is applied. The preparation of the skin is uncomfortable to the patient and unsightly whenever hair must be removed and electrolyte cream applied. The above-described conventional electrodes are invasive and take from 5 to 10 minutes to apply. As a result, the conventional electrodes are not desirable in commercial applications where the patient would visit the establishment only for a short time. The above-described conventional electrodes along with a non-conventional self-preparing electrode having a radically different design from the present invention are discussed in U.S. Pat. No. 4,631,120.

SUMMARY OF THE INVENTION

It is an object of the present invention to provide an EEG head set easy and quick to apply to the head of a patient which is not intimidating or offensive to the patient.

It is an additional object of the present invention to provide a disposable self-preparing monitor which penetrates a caratinaceous layer of skin to provide good electrical contact without causing bleeding or discomfort.

It is another object of the present invention to provide a non-invasive EEG monitor.

The above objects can be obtained by an adjustable head set which is held in place on the back of the patient's head when the patient leans back against a chair head rest. The head set includes disposable monitors that provide good contact with the patient's head without prior skin preparation. The monitors are held in adjustable holders that allow the placement and contact force to be adjusted. The monitors are filled with an electrolyte solution using a disposable applicator.

These together with other objects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 illustrates one embodiment of the head set 100 according to the present invention which includes a disposable monitor 300;

FIG. 2 depicts the detail of the disposable monitor holder 200 of FIG. 1;

FIG. 3 illustrates in greater detail an embodiment of the disposable monitor 300 illustrated in FIG. 2;

FIGS. 4–7 are alternate embodiments of the disposable monitor 300;

FIG. 13 illustrates the details of the holder 800 depicted in FIGS. 10–12;

FIG. 14 illustrates a disposable electrolyte applicator 1000 as used with the disposable monitors 300.

DESCRIPTION OF THE PREFERRED EMBODIMENTS

Figure 7:
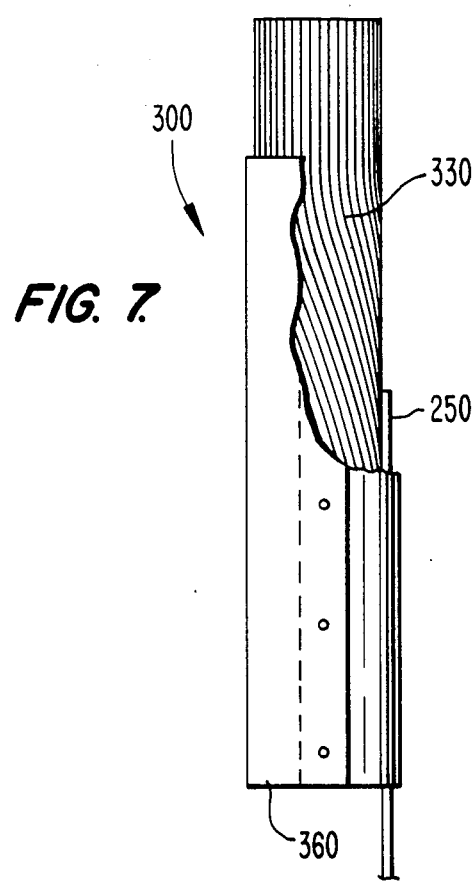

An adjustable head set 100 according to the present invention which includes a holder 200 for a disposable monitor 300 is illustrated in FIG. 1. The head set 100 includes PLEXIGLASS (a synthetic resin material) springs 110 and 120 approximately 0.030 inches thick and 1 inch wide. Spring 110 is 8-13/18 inches long and molded into a semicircle 5 inches in diameter while spring 120 is approximately 4¼ inches long and includes a bend with a semicircle diameter of 5 inches. The springs 110 and 120 are bonded to each other using a PLEXIGLASS (a synthetic resin material) welding compound such as trichlorethylene. The springs 110 and 120 can be of spring steel or another metal, however, the PLEXIGLASS (a synthetic resin material) is preferred because it is less intimidating to the patient. The end of each spring includes a slot 130 5/16 inches wide and 1¼ inches long that can be used for adjusting the placement of the monitors 300 on the head. The head set 100 is bonded to a styrofoam cushion 400 which provides a cushion for the patient's head when it rests against a surface such as a head rest in a chair.

FIG. 2 illustrates the details of the holder 200 of FIG. 1. The monitor 300 frictionally fits into a hole 210 0.152 inches in diameter and ⅜ inches deep drilled in the threaded portion of a 5/16 inch plastic bolt 220. A contact lead wirehole 0.052 inches in diameter is drilled in the other end of the bolt 220 the two holes result in the production of a threaded tube. The threaded portion of the bolt 220 is held in place on the spring 110/120 by plastic nuts 230 and 240. The plastic nuts 230 and 240 allow the threaded bolt 220 to be adjusted toward and away from the patient. This adjustment will either move the monitors 300 into contact with a patient's head which is smaller than the head set 100 or will increase the application force when the patient's head is the proper size. The monitor 300 frictionally fits within hole 210 and contacts silver or silver coated lead wire 250 mounted inside hole 210. In place of the exposed portion of the lead wire 250 contacting the monitor 300, a conductive silver coated sleeve soldered to the lead wire could be used. It is also possible to provide disposable holders 200 with fixed monitors 300 by silver soldering the exposed portion of lead wire 250 to the monitor 300 prior to insertion in hole 210. The portion of the wire 250 emerging from the backside of the holder 200 is insulated and could be provided with a shield to reduce environmental noise.

The monitor 300 comprises a copper rod 310 0.125 inches in diameter and 0.5 inches long including a silver coating 320 approximately 200 microinches thick on both the outside of the rod and inside a hole 340 approximately 0.089 inches in diameter and ⅜ inches deep drilled into one end of the rod 310 forming a tube. The silver coating is applied by a conventional electroplating technique and is preferred to uncoated copper because polarization of the monitor does not occur. Into the hole is inserted approximately 60 twisted silver wires 330 5 mils in diameter. The bundle of twisted silver wires 330 is frictionally fit within the rod 310. The bundle of wires is prepared by wrapping a cylinder with silver wire, cutting the wrap along the axis of the cylinder, folding the bundle and imparting a slight twist to the bundle. This method of bundle preparation ensures that the wires form a flat even tip. To obtain good saturation of the wires with an electrolyte solution, the wires are not bonded to the interior of the rod 310 so that the electrolyte solution will be pulled up into the spaces between the wires by a wicking action. It is possible to silver solder the wires 330 into hole 340, however, the silver solder will occupy space which would normally include electrolyte and therefore the hole in the rod must be deeper. The soldering of the wires 330 into hole 340 will reduce electrical capacitance but does not significantly reduce resistance. If the desired measurements require reduced capacitance, the soldering is recommended. It is important that the exposed end of silver wires 330 be flat so that when the wires contact the skin of the patient essentially all the wires will contact at the same time. The flat surface created by the exposed wire ends acts as a spring type cushion so that extensive penetration of the scalp does not occur. If the exposed ends do not form a flat surface and individual wires are sticking up from the surface unneeded discomfort will be caused by the needle shaped exposed wires. The use of more or less than 60 wires results in a tip that is too rigid or too soft, respectively. It is possible to have silver coated brass or copper wires, however, the increased stiffness of coated wires is not desirable.

FIG. 4 illustrates an alternate version of the monitor that does not include the silver wires. The monitor of FIG. 4 does not provide as good electrical contact as the monitor of FIG. 3.

Another version of the monitor in which the rod 310 has a flared tip 350 is shown in FIG. 5. The flared tip 350, created by pressing the rod 310 against a drill, provides a relatively sharp edge to the rod 310 so that it will penetrate the caratinaceous layer of skin when applied. However, the sharp edge of the monitor can cause patient discomfort.

FIG. 6 illustrates the rod 310 of FIG. 5 with a silver coating 320. As discussed above, the rod 310 is copper, however, other conductive metals such as brass and aluminum can be used.

An alternate version is illustrated in FIG. 7. This monitor 300 is created using paint brush assembly techniques where a conductive or non-conductive sheet 360 is wrapped around the bundle of wires 330 and the lead wire 250 forming a tube. It is also possible to create a monitor 300 by stuffing wires 300 into a plastic rod or tube the way bristles are stuffed into a hair brush.

Figure 8:
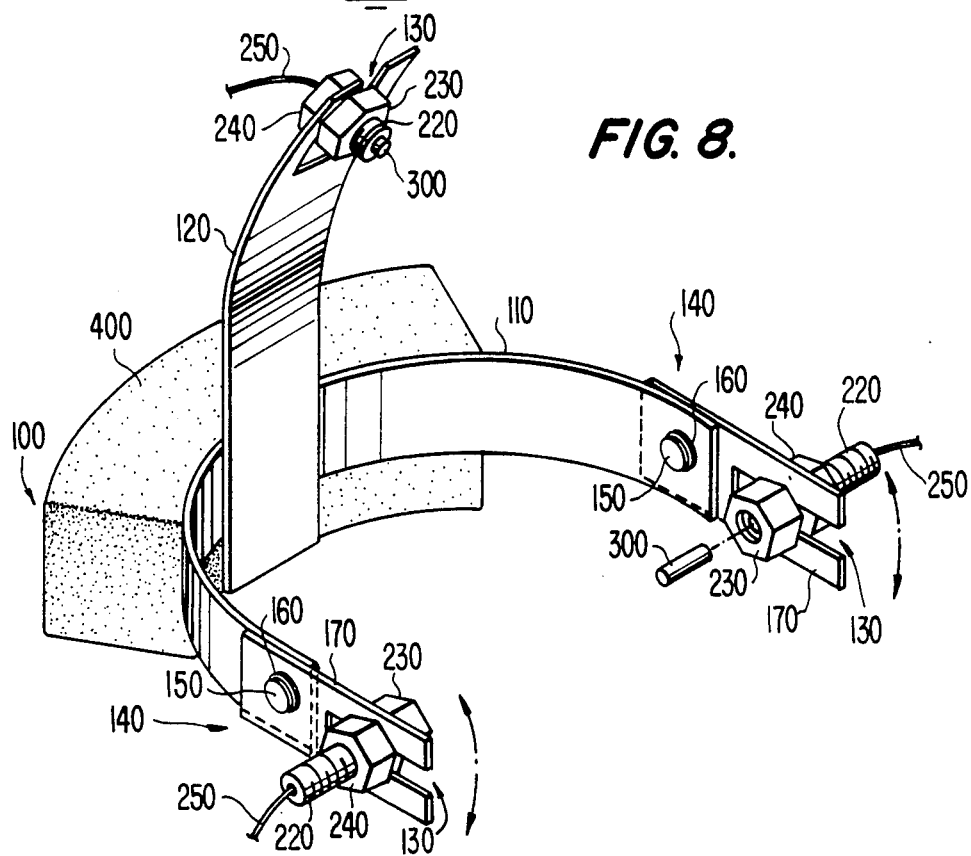
FIG. 8 illustrates a second embodiment of the head set 100 according to the present invention.

FIG. 8 depicts an alternate version of the head set 100 which includes hinges 140 that allow the placement of the monitor to be adjusted in an additional direction. Each hinge 140 includes a rivet 150 and two washers 160 around which the monitor portion 170 of the spring 110 is pivoted.

Figure 9:
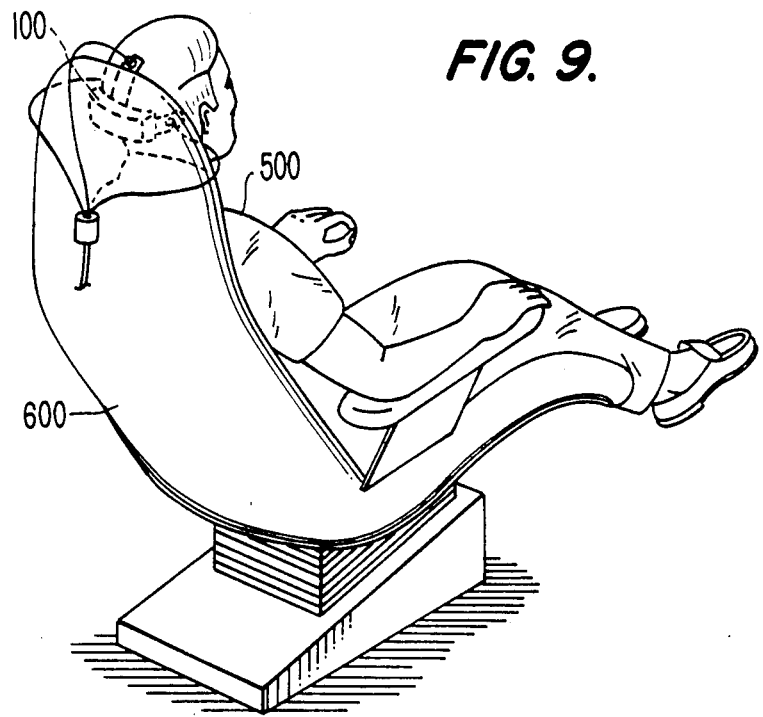
FIG. 9 illustrates how the head set 100 of FIGS. 1 and 7 are used with a patient.

FIG. 9 illustrates how the head set 100 is applied to a patient 500 sitting in a chair 600. After an electrolyte solution is applied to the monitors the head set 100 is placed on the patient's head with the top electrode placed at the international electrode placement position designated $O_z$ and the two side electrodes are placed over the mastoids, and the patient then leans back comfortably in the chair. It takes less than one minute to insert unused monitors 300, apply the electrolyte solution to the monitors 300 and place the head set on the patient's head. If any adjustments to the placement of the electrodes are necessary, the patient need only lean his head forward so that a doctor or technician can make the necessary adjustments. The head set 100 has the monitors in positions for EEG measurements associated with vision testing in an evoked potential autorefractometry system for which the head set 100 was primarily designed. However, the head set 100 can accommodate different type measurements and evoked potential tests by rearranging the relationship of the springs or adding new springs.

Figure 10:
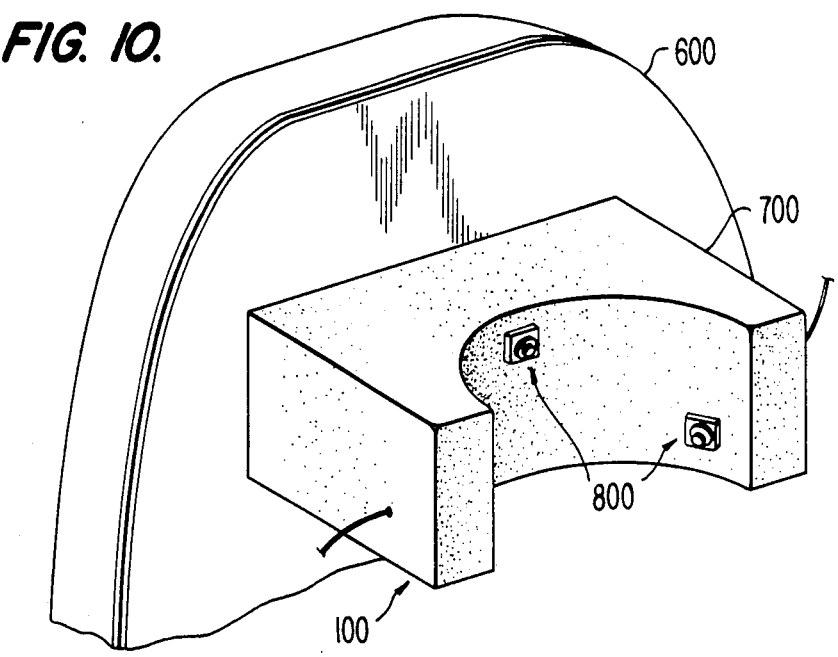
FIG. 10 illustrates an alternate version of the head set 100 as an integrated part of a patient's chair 600.
Figure 11:
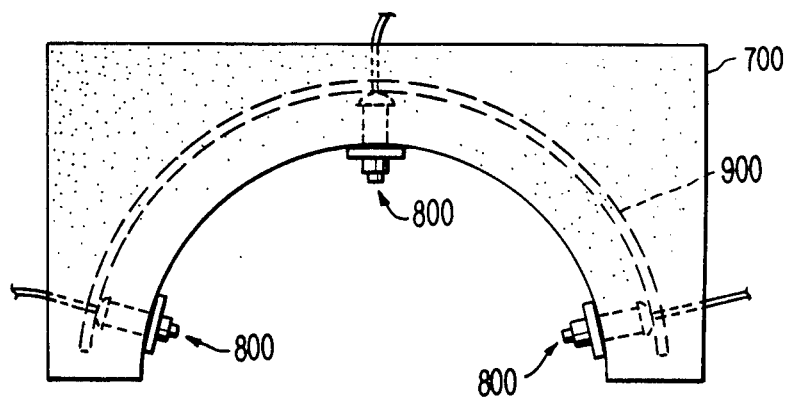
FIGS. 11 and 12 illustrate the details of the integrated head set 100.
Figure 12:
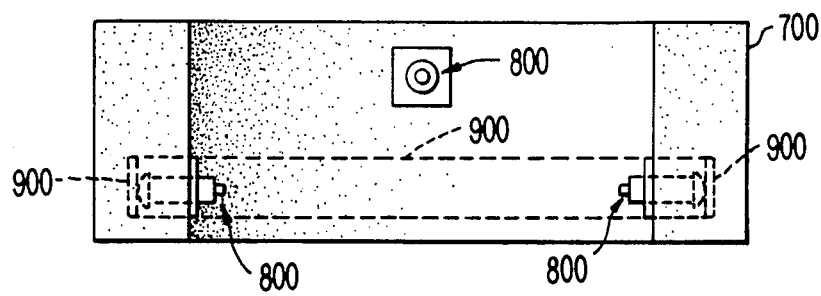

FIG. 10 illustrates an alternate embodiment of the head set 100 as an integrated part of the chair 600. In this embodiment a foam cushion 700 approximately 10 by 6 by 4 inches in size has monitor holders 800 mounted therein. The monitor holders 800 penetrate the cushion as illustrated in FIG. 10 and the bottom pair of holders contact and rest against PLEXIGLASS (a synthetic resin material) spring 900 embedded in cushion 700. The spring 900 is a strip of PLEXIGLASS (a synthetic resin material) approximately 0.030 inches thick, 1 inch wide and 12 inches long bent into the general shape of a human head using a radius of approximately 4 inches. FIGS. 11 and 12 show the placement of the spring 900 in association with the holders 800. In this embodiment, the patient merely rests his head against the backrest and the monitors contact the appropriate portions of the head.

FIG. 13 provides a detailed view of the holder 800 and monitor 300 in this embodiment. The holder 800 comprises the non-threaded portion 810 of a 5/16 inch plastic bolt including a hole 820 for receiving the monitor 300. The bolt 810 also includes a lead wire hole 830 through which the lead wire for the monitor 300 passes. A stabilization plate 840 which frictionally fits on the bolt 810 rests against the interior surface of cushion 700 and provides lateral stability to the monitor so that it does not rock around and get displaced when in contact with the patient's head.

When applying an electrolyte solution, such as water and sodium chloride, to the monitors 300, a disposable electrolyte applicator 1000 is used which comprises a plastic rod 1010 having a hole 1020 filled with the electrolyte solution, as illustrated in FIG. 14. The hole 1020 is covered by a puncturable plastic film 1030 which is penetrated by the monitor 300 after it is mounted in a holder.

Figure 15:
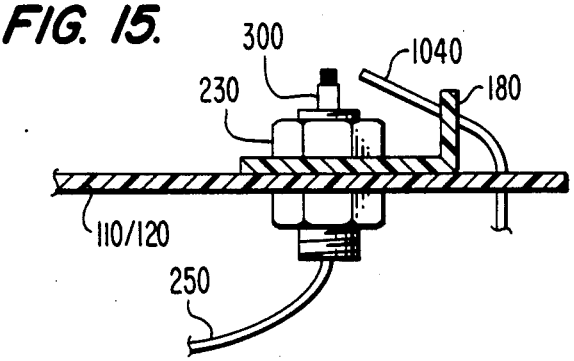
FIG. 15 illustrates an electrolyte solution applicator integrated with the head set 100 of FIGS. 1 and 8.

FIG. 15 illustrates an alternate method of applying the electrolyte solution to the monitor 300. An electrolyte solution tube 1040 is held in proximity to the monitor 300 tip by a tube holder 180 made from bent plexiglass or wire. The electrolyte solution is discharged from tube 1040 after the monitors are in position on the patient's head.

The many features and advantages of the invention are apparent from the detailed specification and thus, it is intended by the appended claims to cover all such features and advantages of the invention which fall within the true scope and spirit thereof. Further, since numerous modifications and changes will readily occur to those skilled in the art, it is not desired to limit the invention to the exact construction and operation illustrated and described, and, accordingly, all suitable modifications and equivalents may be resorted to, falling within the scope of the invention.

We claim:

1. A disposable monitor, comprising:
   a conductive tube; and
   conductive wires contacting and extending from said tube for contacting a patient, said wires being silver and said tube being silver coated.

2. A disposable monitor, comprising:
   a conductive tube; and
   conductive wires contacting and extending from said tube for contacting a patient, wire ends of said wires extending from said tube forming a planar contact surface for contacting the patient.

3. A disposable monitor comprising:
   a conductive tube; and
   an adjustable holder comprising an externally threaded tube frictionally holding said conductive tube, said conductive tube extending from said threaded tube, a pair of nuts threadingly engaging the threaded tube and for adjusting said threaded tube and contact means for electrically contacting the conductive tube.

4. A disposable monitor for an electroencephalographic head set used to obtain measurements from a patient's head in an evoked potential autorefractometry system, said monitor comprising:
   a tube; and
   a silver wire bundle frictionally engaging an interior of said tube where the wires in said bundle are twisted and said bundle extending from said tube to form a planar contact surface for contacting the patient's head at an end of said bundle extending from said tube.

5. A monitor as recited in claim 4, wherein said tube is non-conductive and said monitor further comprises a lead wire in electrical contact with said bundle.

* * * * *